(12) United States Patent
Gunura et al.

(10) Patent No.: US 10,537,459 B2
(45) Date of Patent: Jan. 21, 2020

(54) LEG UNIT FOR A WEARABLE SITTING POSTURE ASSISTING DEVICE

(71) Applicant: Noonee AG, Zurich (CH)

(72) Inventors: Keith Gunura, Zurich (CH); Daniel Vafi, Zurich (CH); Robin Jergen, Adliswil (CH); Simon Hutter, Au (CH)

(73) Assignee: Noonee AG, Zurich (CH)

(*) Notice: Subject to any disclaimer, the term of this patent is extended or adjusted under 35 U.S.C. 154(b) by 0 days.

(21) Appl. No.: 16/097,334

(22) PCT Filed: May 3, 2017

(86) PCT No.: PCT/EP2017/060498
§ 371 (c)(1),
(2) Date: Oct. 29, 2018

(87) PCT Pub. No.: WO2017/191173
PCT Pub. Date: Nov. 9, 2017

(65) Prior Publication Data
US 2019/0133805 A1 May 9, 2019

(30) Foreign Application Priority Data
May 4, 2016 (EP) .................................... 16168341

(51) Int. Cl.
*A61F 5/01* (2006.01)
*A61H 3/00* (2006.01)
*A47C 9/02* (2006.01)

(52) U.S. Cl.
CPC ............ *A61F 5/0125* (2013.01); *A47C 9/025* (2013.01); *A61F 2005/0155* (2013.01); *A61F 2005/0167* (2013.01)

(58) Field of Classification Search
CPC .. B25J 9/0006; A61H 3/008; A61H 2003/007; A61H 3/00; A61H 1/024;
(Continued)

(56) References Cited

U.S. PATENT DOCUMENTS

| 671,638 A | * | 4/1901 | Slagle | ...................... | A47C 9/10 |
|  |  |  |  |  | 297/4 |
| 699,932 A | * | 5/1902 | Smith | ...................... | A47C 9/10 |
|  |  |  |  |  | 248/397 |

(Continued)

FOREIGN PATENT DOCUMENTS

| JP | 2007-275482 A | 10/2007 |
| JP | 2012-98733 A | 5/2012 |

(Continued)

OTHER PUBLICATIONS

Search Report dated Jul. 4, 2017 issued in corresponding EP patent application No. 16168341.2.

(Continued)

*Primary Examiner* — Alvin J Stewart
(74) *Attorney, Agent, or Firm* — Posz Law Group, PLC

(57) ABSTRACT

A leg unit for a wearable sitting posture assisting device, comprises an upper support designed to receive a weight force of a person, a lower support designed to transmit the person's weight force to a ground, a joint connecting the at least two supports to each other, and a blocking means implementing a blocked state to block the joint at at least one sitting angle corresponding to an at least partly sitting posture, the leg unit comprising a guiding means for the blocking means, which guiding means is designed to allow a rotation of the joint while the blocking means is in the blocked state, to a wearable sitting posture assisting device, comprising two of these leg units, and to a method to block such a wearable sitting posture assisting device in an at least partly sitting posture.

15 Claims, 5 Drawing Sheets

Figure 1:
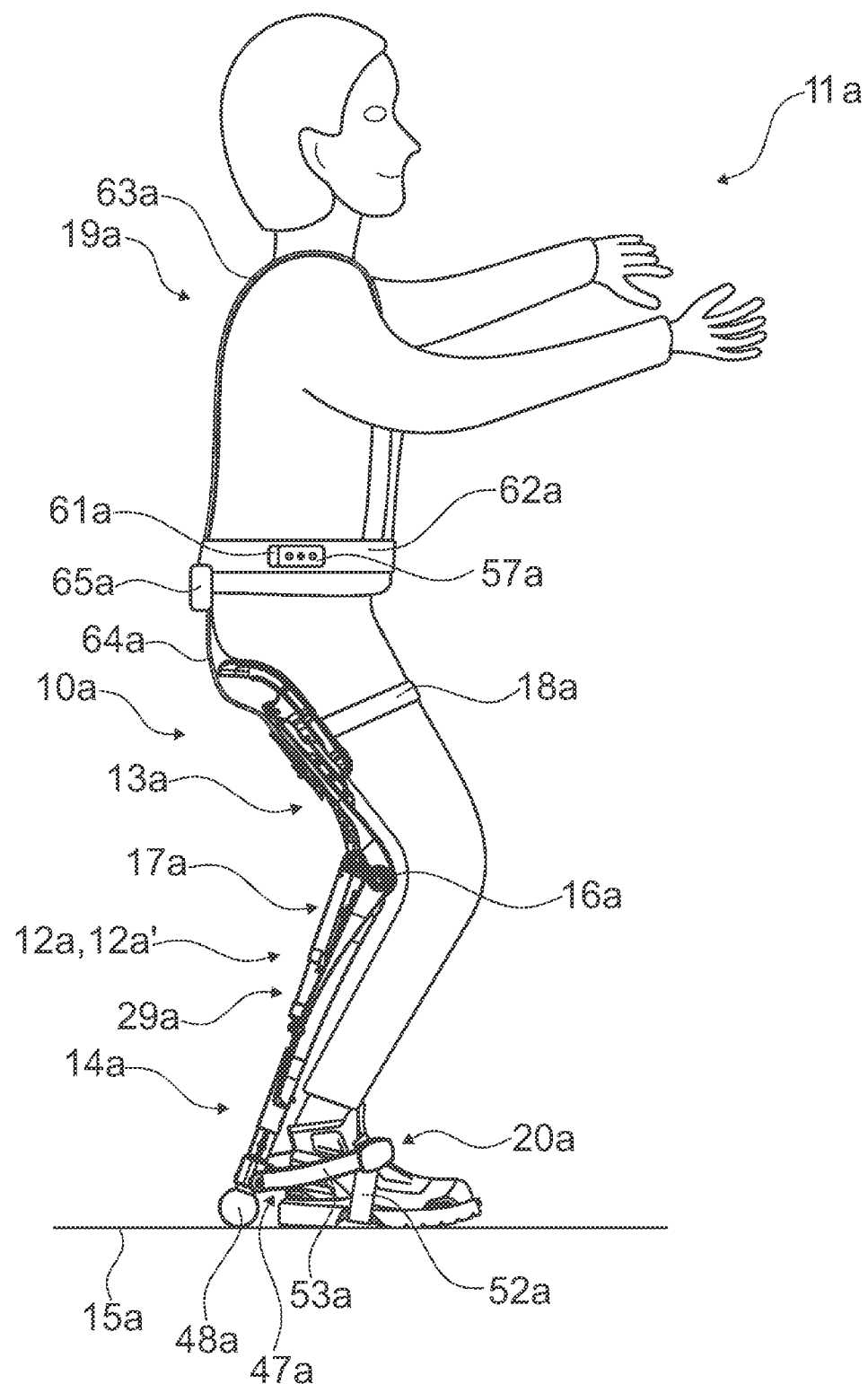

(58) Field of Classification Search
CPC .. A61H 1/0237; A61H 1/0244; A61H 1/0262; A61H 2205/06; A61H 2201/018; A61H 2201/1445; A61F 2/68; A61F 2002/6818; A61F 2002/6845
See application file for complete search history.

(56) References Cited

U.S. PATENT DOCUMENTS

| | | | | |
|---|---|---|---|---|
| 2,099,345 A * | 11/1937 | Olszanowski | A47C 9/10 297/4 |
| 4,138,156 A * | 2/1979 | Bonner | A47C 9/10 297/4 |
| 5,927,797 A * | 7/1999 | Ferguson | A47C 7/029 297/4 |
| 7,662,120 B2 * | 2/2010 | Hiki | A61H 3/008 602/16 |
| 7,731,673 B2 * | 6/2010 | Hiki | A61H 1/0237 602/16 |
| 7,854,715 B2 * | 12/2010 | Ashihara | A61F 5/0102 135/65 |
| 7,887,136 B2 * | 2/2011 | Zoell | A47C 9/025 297/284.3 |
| 7,938,791 B2 * | 5/2011 | Shishido | A61H 3/008 601/5 |
| 7,947,004 B2 * | 5/2011 | Kazerooni | A61B 5/1038 602/16 |
| 8,002,719 B2 * | 8/2011 | Ashihara | B25J 9/0006 601/33 |
| 8,083,695 B2 * | 12/2011 | Ashihara | A61F 5/01 601/33 |
| 8,114,034 B2 * | 2/2012 | Ikeuchi | A61H 3/00 601/5 |
| 8,142,371 B2 * | 3/2012 | Ikeuchi | A61H 3/008 601/23 |
| 8,202,234 B2 * | 6/2012 | Ikeuchi | A61H 3/008 601/23 |
| 8,303,524 B2 * | 11/2012 | Ikeuchi | A61H 3/008 482/66 |
| 8,388,558 B2 * | 3/2013 | Matsuoka | A61H 3/008 601/35 |
| 8,403,408 B2 * | 3/2013 | Hosler | A47C 9/025 297/4 |
| 8,523,790 B2 * | 9/2013 | Matsuoka | A61H 3/008 601/35 |
| 8,679,041 B2 * | 3/2014 | Noda | A61H 3/008 128/846 |
| 8,968,222 B2 * | 3/2015 | Kazerooni | B25J 9/0006 224/265 |
| 8,968,223 B2 * | 3/2015 | Ikeuchi | A61H 3/008 601/23 |
| 10,271,660 B2 | 4/2019 | Gunura | A47C 9/025 |
| 2003/0093018 A1 | 5/2003 | Albrecht et al. | |
| 2005/0279796 A1 * | 12/2005 | Chu | A45F 3/08 224/637 |
| 2006/0052731 A1 * | 3/2006 | Shimada | A61F 5/0102 602/5 |
| 2006/0270951 A1 * | 11/2006 | Ikeuchi | A61H 3/00 601/5 |
| 2007/0233279 A1 * | 10/2007 | Kazerooni | A61F 2/68 623/24 |
| 2008/0009778 A1 * | 1/2008 | Hiki | A61F 5/0102 602/16 |
| 2008/0161937 A1 * | 7/2008 | Sankai | A61H 3/008 623/25 |
| 2008/0234608 A1 * | 9/2008 | Sankai | A61B 5/04888 601/5 |
| 2009/0036815 A1 * | 2/2009 | Ido | A61H 1/0237 602/23 |
| 2009/0099494 A1 * | 4/2009 | Ashihara | A61H 3/008 602/23 |
| 2009/0281636 A1 * | 11/2009 | Kudoh | A61H 3/008 623/32 |
| 2009/0292232 A1 * | 11/2009 | Ashihara | A61H 3/008 602/23 |
| 2009/0312844 A1 * | 12/2009 | Ikeuchi | A61H 3/008 623/40 |
| 2010/0076360 A1 * | 3/2010 | Shimada | A61B 5/1038 602/23 |
| 2010/0094182 A1 * | 4/2010 | Noda | A61H 3/008 601/35 |
| 2010/0094188 A1 * | 4/2010 | Goffer | B25J 9/0006 602/23 |
| 2010/0114330 A1 * | 5/2010 | Shishido | A61H 3/008 623/27 |
| 2010/0121232 A1 * | 5/2010 | Sankai | A61H 3/008 601/23 |
| 2010/0130894 A1 * | 5/2010 | Ikeuchi | A61H 3/008 601/34 |
| 2010/0145239 A1 * | 6/2010 | Kudoh | A61H 3/008 601/34 |
| 2010/0204621 A1 * | 8/2010 | Ashihara | A61H 3/008 601/34 |
| 2010/0210980 A1 * | 8/2010 | Kudoh | A61H 3/008 601/34 |
| 2010/0227741 A1 * | 9/2010 | Rosenberg | A61F 5/0123 482/79 |
| 2010/0271051 A1 * | 10/2010 | Sankai | A61B 5/1038 324/679 |
| 2011/0004322 A1 * | 1/2011 | Sankai | A61H 3/008 623/25 |
| 2011/0257567 A1 * | 10/2011 | Ikeuchi | A61H 3/008 601/35 |
| 2011/0306907 A1 * | 12/2011 | Ashihara | A61H 3/008 601/35 |
| 2013/0006159 A1 * | 1/2013 | Nakashima | A61H 1/024 602/23 |
| 2013/0102934 A1 * | 4/2013 | Ikeuchi | A61H 3/00 601/35 |
| 2014/0138995 A1 * | 5/2014 | Leib | A61G 5/14 297/283.2 |
| 2014/0276264 A1 * | 9/2014 | Caires | A61H 3/00 601/34 |
| 2015/0272810 A1 * | 10/2015 | Teng | A61H 1/024 601/34 |
| 2016/0113831 A1 * | 4/2016 | Hollander | A61H 1/0244 623/31 |
| 2016/0175180 A1 * | 6/2016 | Bond | A61H 3/00 602/23 |
| 2016/0213549 A1 * | 7/2016 | Iida | A61H 1/024 |
| 2016/0331486 A1 * | 11/2016 | Nakatani | A61H 3/00 |
| 2016/0331625 A1 * | 11/2016 | Sankai | B25J 9/0006 |
| 2018/0235830 A1 * | 8/2018 | Rokosz | A61H 3/00 |
| 2018/0257216 A1 * | 9/2018 | Shavit | A61H 1/0255 |
| 2018/0304456 A1 * | 10/2018 | Gunura | A47C 9/025 |
| 2018/0317662 A1 * | 11/2018 | Gunura | A47C 9/025 |
| 2018/0353791 A1 * | 12/2018 | Hugou | A63B 21/0023 |
| 2019/0070059 A1 * | 3/2019 | Dalley | A61H 3/00 |
| 2019/0125551 A1 * | 5/2019 | Hummelshoj | A61F 2/604 |
| 2019/0125613 A1 * | 5/2019 | Kim | A61H 3/00 |

FOREIGN PATENT DOCUMENTS

| | | |
|---|---|---|
| JP | 2013-111378 A | 6/2013 |
| JP | 2015-198736 A | 11/2015 |
| KR | 20120062375 A | 6/2012 |
| WO | 03/044765 A2 | 5/2003 |

OTHER PUBLICATIONS

International Preliminary Report on Patentability dated Apr. 17, 2018 issued in corresponding International Patent Application No. PCT/EP2017/060498 (English translation only).
Office Action dated Jul. 30, 2019 issued in corresponding JP patent application No. 2018-557869 (and English translation).

(56) References Cited

OTHER PUBLICATIONS

Office Action dated Jul. 15, 2019 issued in corresponding KR patent application No. 10-2018-7034809 (and English summary).

* cited by examiner

LEG UNIT FOR A WEARABLE SITTING POSTURE ASSISTING DEVICE

CROSS REFERENCE TO RELATED APPLICATIONS

This application is a U.S. national stage application of PCT/EP2017/060498 filed on May 3, 2017, which is based on European Patent Application No. 16168341.2 filed on May 4, 2016, the contents of which are incorporated herein by reference.

STATE OF THE ART

The invention relates to a wearable sitting posture assisting device.

A wearable sitting posture assisting device is already known from document WO 2015/028373 A1.

The objective of the invention is, in particular, to simplify an embodiment of a leg unit of the posture assisting device without reducing reliability. The objective is achieved according to the invention by the features of patent claim 1, while advantageous embodiments and further developments of the invention may be gathered from the subclaims and the further independent claims.

Advantages of the Invention

By the invention, a leg unit for a wearable sitting posture assisting device is proposed, comprising an upper support designed to receive a weight force of a person, a lower support designed to transmit the person's weight force to a ground, a joint connecting the at least two supports to each other, and a blocking means implementing a blocked state to block the joint at at least one sitting angle which corresponds to an at least partly sitting posture, further comprising a guiding means for the blocking means, which guiding means is designed to allow a rotation of the joint while the blocking means is in the blocked state. By such a guiding means a person wearing a sitting posture assisting device with such a leg unit can get up without a necessity of unblocking the blocking means. An electronic control unit to unblock the blocking means when the person gets up may be dispensed with. A controlling of the leg unit, especially of the blocking means, may be simplified. As a result of this a high reliability of the leg unit can be achieved. In addition an implementation of the blocking means and a controlling of the blockings means can be simplified. A "wearable sitting posture assisting device" is herein to be understood as a device which is designed to receive a weight force of a person in a sitting posture or in a partly sitting posture and to transmit the person's weight force to a ground. A "blocking means" is herein to be understood as a means provided to transmit a person's weight force received by the upper support to the lower support. In particular the blocking means is designed to rigidly connect the lower support and the upper support to each other in the blocked state. A "guiding means" is herein to be understood as a means designed to allow an at least delimited movement of the upper support and the lower support with respect to each other while the blocking means is in the blocked state. "Provided" is herein to be understood, in particular, as specifically programmed, designed and/or equipped.

It is further proposed that the blocking means has an adjustable length provided to define the at least partly sitting posture. Thus the sitting angle for the at least partly sitting posture can be mechanically stored by the blocking means while a movability of the joint is provided by the guiding means. By storing the sitting angle in the blocking means the person can walk while wearing the sitting posture assisting device without losing the stored sitting angle. Thus the person can take the same at least partly sitting posture as before after changing his location. A comfort while wearing the sitting posture assisting device can be increased.

In a preferred embodiment, in the blocked state, the length of the blocking means is at least substantially fixed. This allows easily defining the sitting angle the person wishes to take. Preferably the length of the blocking means directly corresponds to the sitting angle. A "sitting angle" can herein be understood as an angle between the upper support and the lower support, wherein the sitting angle has its minimum at a standing posture and its maximum at a fully sitting posture. Preferably a fully stretched state of the leg unit corresponds to the sitting angle of zero degrees. The maximum sitting angle can be within a range of 70 degrees to 100 degrees. By "at least substantially fixed" can herein be understood that the blocking means is springy while being in the blocked state, for example if the blocking means is designed pneumatically, which leads to a compressible length if the blocking means is in the blocked state. "At least substantially fixed" means in particular that the length is variable by at most 10 percent of the length if the person's weight force is applied. By having a blocking means the length of which is only substantially fixed, a damping means for the guiding means can easily be provided.

Alternatively it is also conceivable that the guiding means comprises a damping means for the blocking means.

It is further proposed that one of the supports comprises a pivot element, on which the blocking means is swivel-mounted. This allows an easy mounting of the blocking means on one of the supports. The blocking means can be swivel-mounted either on the lower support or on the upper support. Preferably the blockings means is swivel-mounted on one of the supports only on one of its ends, wherein "swivel-mounted" should be understood in this context, if nothing else is mentioned, as a mounting that only allows a rotation.

Preferably the guiding means comprises at least one end stop provided to limit the rotation of the joint to the sitting angle which the blocking means is adjusted to. This allows limiting the rotation of the joint connecting the supports to the sitting angle stored in the blocking means. An "end stop" can herein be understood as a mechanical limitation of a movement of the blocking means, which movement is provided by the guiding means.

In a preferred embodiment the leg unit comprises an expansion element, which is provided to tension the blocking means between the end stop of the guiding means and the pivot element. In this way, the blocking means can be kept in contact with the end stop as long as the blocking means is in the unblocked state. If the blocking means is switched to the blocked state, the actual sitting angle will be stored. Afterwards the blocking means and the guiding means with its end stop are capable of transmitting the person's weight force from the upper supports to the lower support, which allows a person to sit on the sitting posture assisting device.

Further it is proposed that the guiding means is provided for reducing the sitting angle. Thus the person can get up without unblocking the blocking means. The guiding means provides a mechanical solution for a security mechanism to keep one's balance. By "reducing the sitting angle" can herein be understood that the guiding means always allows the person to get up but limits the movement when the person sits down to the sitting angle stored in the blocking means.

Preferably the guiding means comprises at least one linear guide designed to connect the blocking means and one of the supports with each other. By a linear guide interacting with the blocking means, the movability provided by the blocking means in the unblocked state can be taken over by the guiding means. Thus a very simple guiding means may be provided.

Further it is proposed that the linear guide comprises at least one contacting surface, which is provided for the blocking means and serves as the end stop that is provided for limiting the rotation of the joint. As such a linear guide only provides a limited movability in comparison to the movability provided by the blocking means in the unblocked state, the limitation to the sitting angle stored in the blocking element can be implemented easily.

In one embodiment the guiding means comprises a guiding element, which is pivotably connected to one of the supports, thus providing the linear guide for the blocking means. By means of an additional guiding element a simple construction can be achieved. A "guiding element" can herein be understood as a part separated from the blocking mean, which guiding element preferably provides the movability of the joint when the blocking means is in the blocked state, by the guiding element connecting the blocking means and one of the supports in such a way that they are movable with respect to each other.

Preferably the linear guide has a main extension direction orientated in parallel to a main extension direction of the blocking means. This allows a very simple construction. In particular such an embodiment allows a simple damping of the end stop, which leads to an increased comfort in wearing the sitting posture assisting device. A "main extension direction" of the blocking means can herein be understood as a direction along which the length of the blocking means is adjustable.

It is proposed that the blocking means comprises at least two blocking elements, wherein one of them is swivel-mounted on one of the supports and another one of them is linearly movable connected with the guiding element. This allows an easy construction with three parts, which are respectively pairwise linearly movable connected to each other, thus allowing a separation of the linear guide and the swivel-mounting of the blocking means on the support.

In a further embodiment it is proposed that one of the supports comprises a base frame providing the linear guide, by which the blocking means is connected to the support movably and pivotably. This allows a very compact construction without requiring additional parts for the guiding means. A small number of parts, especially of movable parts, can be realized.

Furthermore a wearable sitting posture assisting device comprising two leg units is proposed. In addition, a method to block a wearable sitting posture assisting device in an at least partly sitting posture is proposed, in which method a blocking means blocks a joint in an at least partly sitting posture, the joint connecting an upper support, which is designed to receive a weight force of a person, to a lower support, which is designed to transmit the person's weight force to a ground, wherein a guiding means for the blocking means allows a rotation of the joint while the blocking means is in the blocked state.

DRAWINGS

Further advantages may be gathered from the following description of the drawings. In the drawings two exemplary embodiments of the invention are depicted. The drawings, the description and the claims contain a plurality of features in combination. The person having ordinary skill in the art will purposefully also consider the features separately and will find further expedient combinations.

Figure 2:
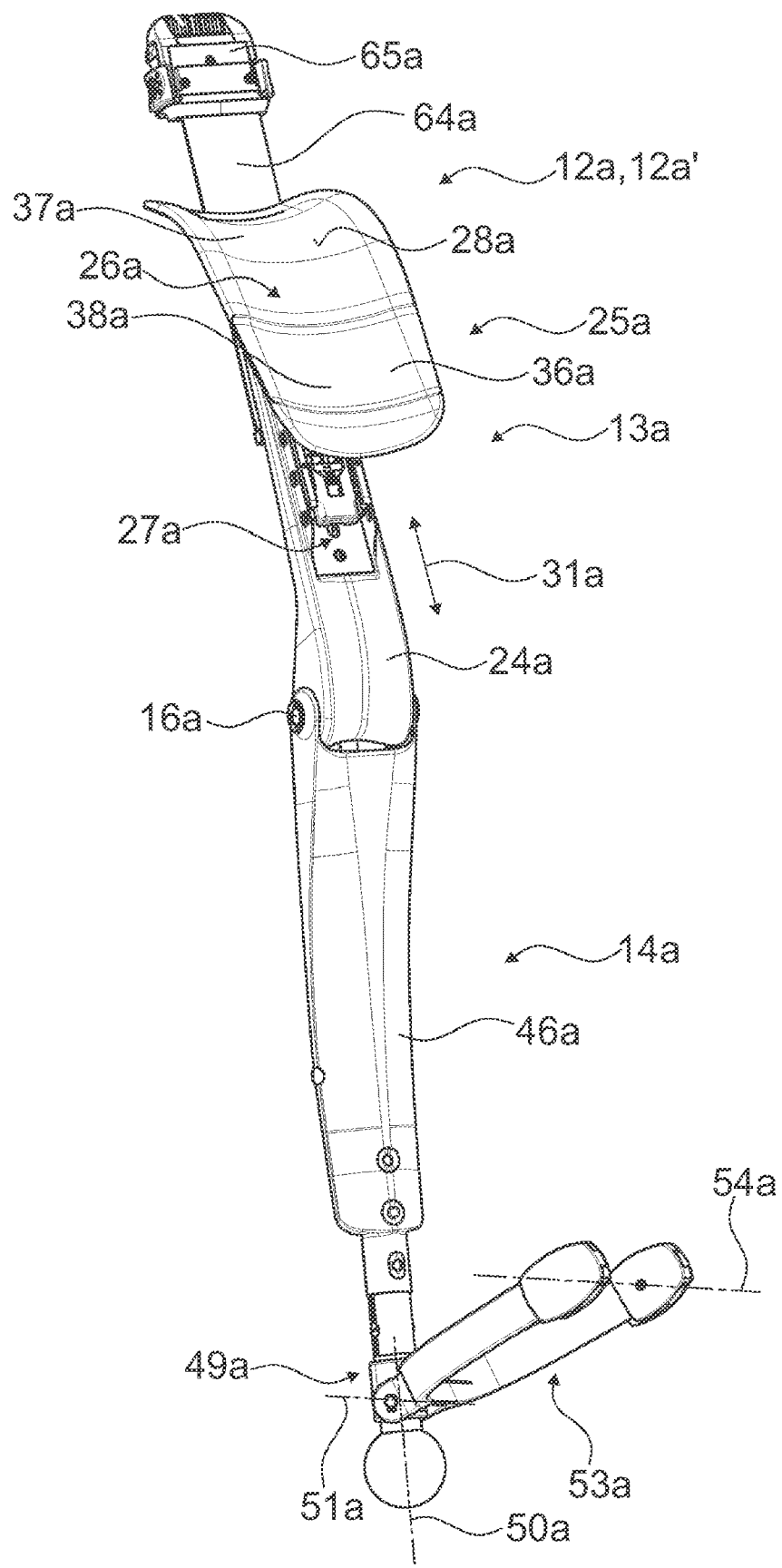
Figure 3:
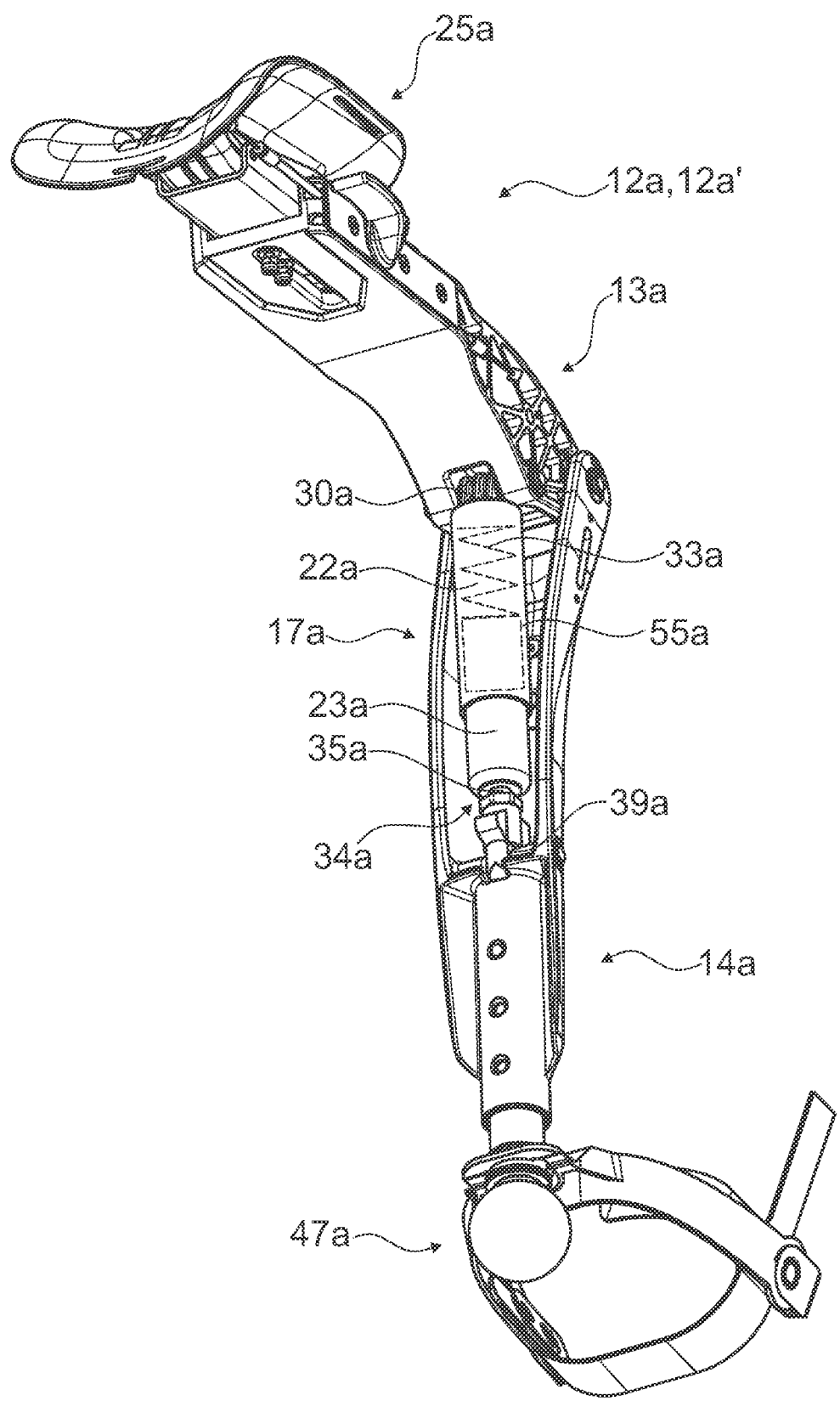
Figure 4:
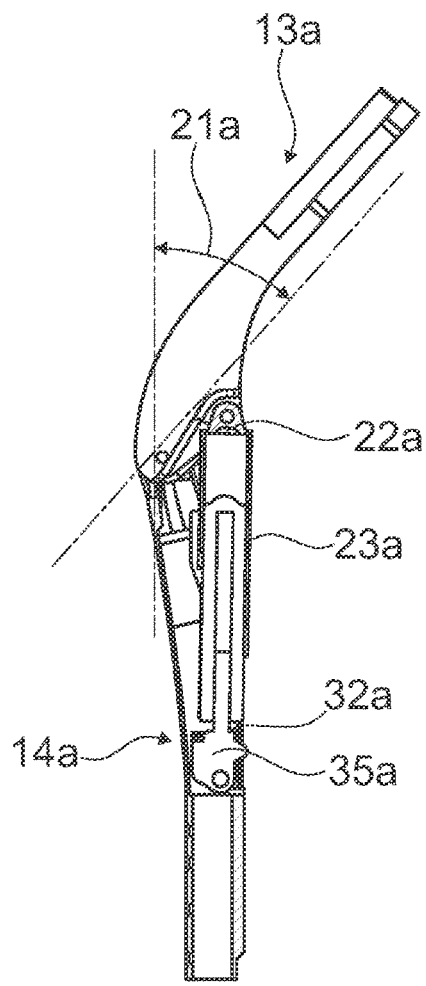
Figure 5:
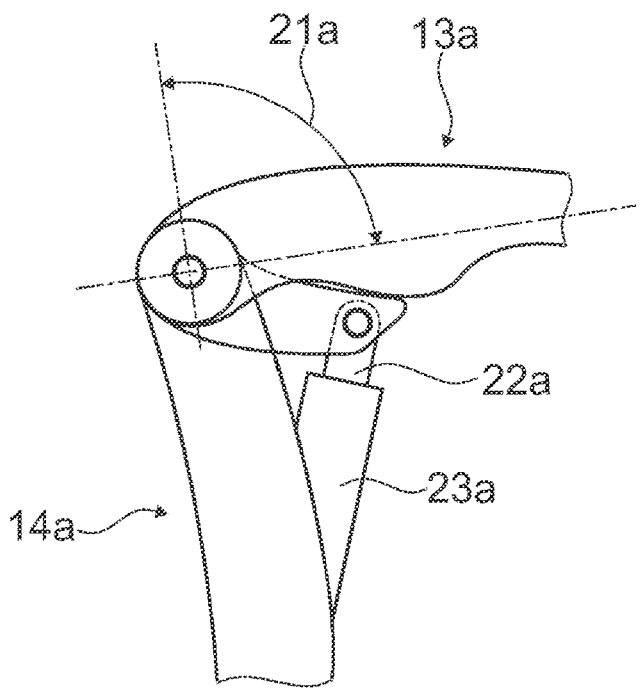
Figure 6:
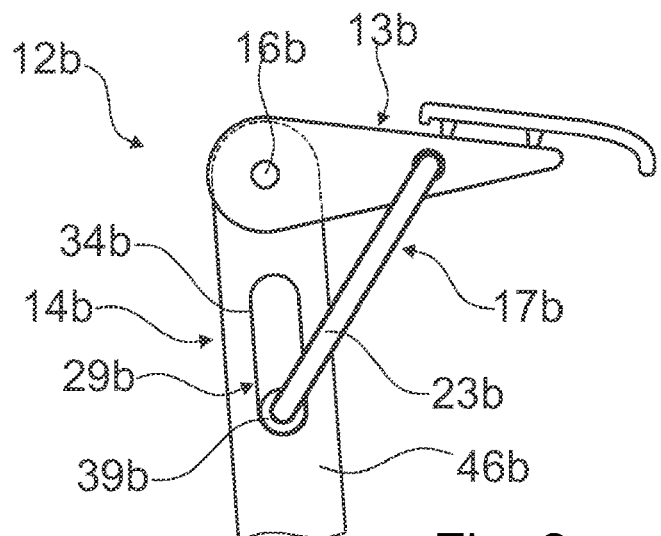
Figure 7:
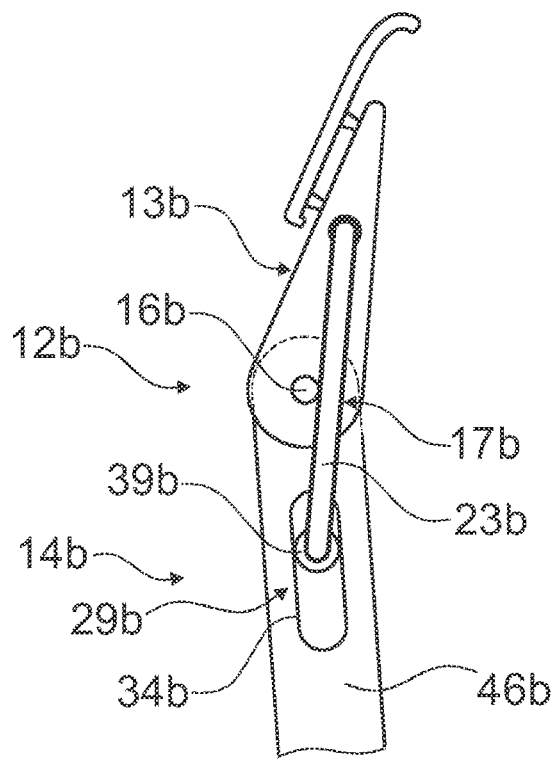
Figure 8:
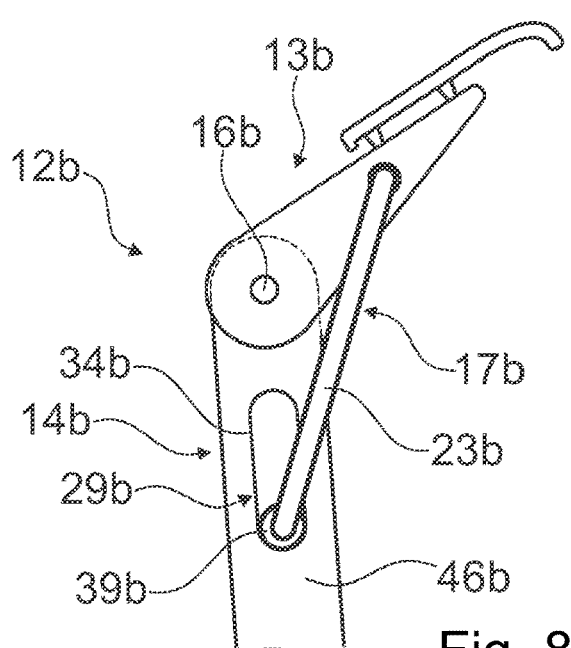

It is shown in:

FIG. 1 a person wearing a wearable sitting posture assisting device,

FIG. 2 a leg unit of the wearable sitting posture assisting device in a perspective view, FIG. 3 the leg unit of FIG. 1 in a rear view, FIG. 4 a blocking means and a guiding means of the leg unit in a schematic representation, FIG. 5 the leg unit of FIG. 4 at a different sitting angle, FIG. 6 a second embodiment of a leg unit with a guiding means, FIG. 7 the leg unit of FIG. 6 at a different sitting angle, and FIG. 8 the leg unit of FIG. 6 at a further different sitting angle.

DESCRIPTION OF EXEMPLARY EMBODIMENTS

FIG. 1 shows a wearable sitting posture assisting device 10a, which is designed to assist a person 11a when taking a sitting or partly sitting posture. The sitting posture assisting device 10a is designed to be used in a sitting posture, in a partly sitting posture and in a walking mode. The wearable sitting posture assisting device 10a features a blocked state, in which the sitting posture assisting device 10a assists the person 11a wearing the sitting posture assisting device 10a when taking the sitting or the partly sitting posture, and an unblocked state, in which the person 11a can walk while wearing the sitting posture assisting device 10a. The wearable sitting posture assisting device 10a has two leg units 12a, 12'a, each provided to be connected to a respective one of a person's legs. The leg units 12a, 12'a are designed equivalently. Because of this, only the leg unit 12a is described in detail.

The leg unit 12a comprises an upper support 13a designed to receive a weight force of the person 11a, a lower support 14a designed to transmit the weight force to a ground 15a, a joint 16a pivotably connecting the upper support 13a and the lower support 14a to each other, and a blocking means 17a to block the joint 16a. The upper support 13a and the lower support 14a are designed to transmit the weight force if the joint 16a is blocked by the blocking means 17a. In the blocked state the weight force of the person 11a is received by the upper support 13a and is transmitted to the lower support 14a by the joint 16a and the blocking means 17a. In the blocked state, the upper support 13a and the lower support 14a form a seat on which the person 11a wearing the sitting posture assisting device 10a can sit.

The upper support 13a and the lower support 14a are each designed to be connected to the respective leg of the person 11a wearing the sitting posture assisting device 10a. In the shown embodiment the upper support 13a comprises a thigh connection means 18a for connecting to a thigh of the person 11a, and a body wearing unit 19a to be worn on a body of the person 11a. The lower support 14a comprises a foot connection unit 20a for connecting to a foot or a shoe of the person 11a. In addition or alternatively, the lower support 14a may comprise a lower leg connection means for connecting to the lower leg of the person. By connecting the lower support 14a to the shoe or to a lower leg and connecting the upper support 13a to the thigh, the sitting posture assisting device 10a follows a movement of the person's 11a leg in the walking mode. The lower support 14a is provided to be arranged to the rear of the person's 11a lower leg. The upper support 13a is provided to be arranged to the rear of the person's 11a thigh. The joint 16a is provided to be arranged to the rear of the person's 11a knee.

The joint 16a forms a knee joint, which is to be placed at least approximately at the same level as the person's 11a knee. While the person 11a is walking, the joint 16a at least approximately follows a movement of the person's 11a knee as an axis of the joint 16a is displaced in relation to an axis of the person's 11a knee. The blocking means 17a is designed to block the joint 16a at different sitting angles 21a. The sitting angle 21a depends on whether the person 11a takes a sitting posture or a partly sitting posture. In the sitting posture the sitting angle 21a between the upper support 13a and the lower support 14a is at least 45 degrees. In the partly sitting posture the sitting angle 21a between the upper support 13a and the lower support 14a is less than 45 degrees. A fully stretched state of the joint 16a corresponds to a sitting angle 21a of zero degrees. The lower the sitting posture is, the greater the sitting angle 21a becomes.

The blocking means 17a comprises two blocking elements 22a, 23a. The blocking means 17a is designed like a hydraulic damper, comprising a cylinder and a piston each functioning as one of the blocking elements 22a, 23a. In the unblocked state the two blocking elements 22a, 23a are movable with respect to each other. In the blocked state the two blocking elements 22a, 23a are rigidly connected to each other. The blocking means 17a is in particular constructed as a hydraulic blocking means. Other embodiments, e.g. a mechanic or an electro-mechanic blocking means, are also conceivable.

The upper support 13a comprises a base frame 24a, which is connected to the lower support 14a by the joint 16a. The base frame 24a forms a first joint element for the joint 16a connecting the upper support 13a and the lower support 14a. The first blocking element 22a is connected to the base frame 24a. The base frame 24a is provided to receive the person's 11a weight force. The weight force acting on the upper support 13a is fully received by the base frame 24a. The weight force is then transmitted from the base frame 24a to the lower support 14a by the blocking means 17a and the joint 16a.

The upper support 13a comprises a seat unit 25a (cf. FIG. 2). The seat unit 25a comprises a sitting means 26a and a frame means 27a. The sitting means 26a is movably mounted on the frame means 27a. The sitting means 26a forms a seat surface 28a. The seat surface 28a is designed to come into contact with the thigh of the person 11a sitting or partly sitting on the sitting posture assisting device 10a. To adapt the sitting means 26a to a person's 11a anatomy, the seat surface 28a is adjustable. To increase a sitting comfort when taking a sitting posture or a partly sitting posture, the seat surface 28a is self-adjusting. The thigh connection means 18a comprises a thigh strap, which is designed to keep the seat surface 28a in contact with the thigh of the person 11a wearing the sitting posture assisting device 10a. The frame means 27a has its main extension direction 31a, which is orientated parallel to a direction along which the sitting means 26a is shiftable with respect to the frame means 27a.

The seat unit 28a is designed to be used in different postures, starting at a standing posture, which corresponds to the sitting angle 21a of zero degrees, down to a sitting posture with a maximum sitting angle 21a of at least 80 degrees and preferably at least 90 degrees. By the way, the maximum sitting angle 21a may also be larger than 90 degrees. The seat unit 25a is designed to be worn in the walking mode as well as when taking a sitting or partly sitting posture. For the different sitting or partly sitting postures, the sitting means 26a of the seat unit 25a provides different sitting positions, in which the person 11a wearing the sitting posture assisting device 10a can sit or partly sit on the sitting means 26a.

The frame means 27a of the seat unit 25a is designed to receive the weight force of the person 11a sitting or partly sitting on the sitting means 26a. If the person sits or partly sits on the sitting posture assisting device 10a, the weight force of the person 11a is transmitted through the sitting means 26a to the frame means 27a of the seat unit 25a. From the frame means 27a of the seat unit 25a the weight force is transmitted to the base frame 24a of the upper support 13a. Further on, the weight force is transmitted from the base frame 24a of the upper support 13a to the joint 16a and to the blocking means 17a connecting the upper support 13a and the lower support 14a, and then is then transmitted to the lower support 14a. Through the lower support 14a the weight force of the person 11a sitting on the sitting posture assisting 10a device is transmitted to the ground 15a. In the shown embodiment, the lower support 14a is, at least in the sitting or partly sitting postures, in contact with the ground 15a. As an alternative, it is also possible that the lower support 14a is designed to transmit the weight force of the person 11a via the person's 11a shoes. In the walking mode, in which the seat unit 25a can be used while the person 11a wearing the sitting posture assisting device 10a is walking or standing, the lower support 14a is at least partly lifted from the ground 15a.

The sitting means 26a is movable on the frame means 27a by a rotatable connection between at least a portion of the sitting means 26a and the frame means 27a of the seat unit 25a. In this way the sitting means 26a is designed for self-adjusting an orientation at least of a portion of the sitting means 26a with respect to the frame means 27a. The rotatable connection between the sitting means 26a and the frame means 27a allows aligning the sitting means 26a with the leg of the person 11a wearing the sitting posture assisting device 10a. Whether the person 11a is sitting or partly sitting depends in particular on the sitting angle 21a enclosed by the upper support 13a and the lower support 14a. When the person 11a is sitting or partly sitting, the weight force of the person 11a forces the sitting means 26a into a position which depends on the sitting angle 21a enclosed by the upper support 13a and the lower support 14a.

The sitting means 26a comprises a sitting element 36a, which forms the seat surface 28a. Depending on a material the sitting element 36a consists of, the sitting means 26a may have a support structure partly supporting or tightening the sitting element 36a. In the shown embodiment the sitting element 36a implements the support structure. As a result of this, the sitting element 36a and the support structure are embodied in a one-part-implementation. Additionally or alternatively the sitting means 26a may contain an additional frame element providing the support structure for supporting or tightening the sitting element 36a. In particular, in such an embodiment the sitting element 36a is provided to be connected to the frame means 27a via the frame element of the sitting means 26a.

The sitting element 36a is designed to be moved between a first sitting position, which is especially intended for the sitting posture, and a second sitting position, which is especially intended for the partly sitting posture, relative to the frame means 27a. The sitting element 36a, which forms the seat surface 28a, is self-adjusting with respect to a rear side of the person's 11a thigh and/or buttock when the person 11a takes the sitting posture or partly sitting posture. The sitting element 36a is provided to be moved continuously between the first sitting position and the second sitting position. In the shown embodiment, the sitting element 36a is made of a stiff material, e.g. a plastic, a carbon composite material or a light metal, to form the seat surface 28a with a dimensionally stable shape. As mentioned before, the sitting element 36a can also be designed to have a flexible shape.

With respect to a cross section in the plane perpendicular to the axis of the joint 16a, the sitting element 36a has a first portion 37a, in which the seat surface 28a has a substantially flat shape, and a second portion 38a, in which the seat surface 28a has a bent shape. The shape of the seat surface 28a is defined along the main extension direction 31a of the upper support 13a. With reference to a transition between these two portions 37a, 38a, the portion 37a, in which the seat surface 28a has the at least substantially flat shape, extends towards the joint 16a connecting the upper support 13a and the lower support 14a. The portion 37a of the sitting element 36a, in which the seat surface 28a has the at least substantially flat shape, is designed to come into contact with the rear side of the person's 11a thigh. This portion 37a is especially intended for the sitting posture. The portion 38a of the sitting element 36a, in which the seat surface 28a has the bent shape, is designed to come into contact with the person's 11a buttock. This portion 38a is especially intended for the partly sitting posture.

When the person 11a wearing the sitting posture assisting device 10a is walking, the sitting element 36a has no more than a loose contact to the thigh and/or the buttock of the person 11a. The sitting element 36a is designed to move on its own to a basic position, which corresponds to the first sitting position. In the basic position, the portion 37a of the seat surface 28a having the flat shape is orientated substantially parallel to the main extension direction 31a of the frame means 27a. As the blocking means 17a is unblocked in the walking mode, the leg unit 12a follows the movement of the person's 11a leg during walking. The thigh connection means 18a and the foot connection unit 20a keep the leg unit 12a in contact with the person's 11a leg. For the different sitting positions, the sitting element 36a is designed to be deflected by at least 5 degrees. In the shown embodiment, the sitting element 36a can be deflected by at least 30 degrees, while a higher deflectability may be also provided. The first sitting position, which is designed for a sitting posture, corresponds to an angle of the sitting element 36a of zero degrees. The first sitting position is especially designed for sitting angles 21a above 50 degrees. The second sitting position, which is designed for a partly sitting posture, corresponds in particular to sitting angles 21a of less than 30 degrees.

The sitting element 36a is designed to be deflected by the weight force of the person 11a sitting on the wearable sitting posture assisting device 10a. The weight force of the person 11a, especially in the partly sitting posture, acts as a torque rotating the sitting element 36a. In the partly sitting posture the weight force acting on the portion 38a of the sitting surface 28a having the bent shape is greater than the weight force acting on the portion 37a of the sitting surface 28a having the flat shape. In the sitting posture the weight force acts the other way round. The torque provided by the person's 11a weight force forces the sitting element 36a into the different sitting positions. As the torque depends on the sitting angle 21a, the sitting position taken by the sitting element 36a depends on the sitting angle 21a. A deflection of the sitting element 36a is restricted by at least one stopping element. A range of the sitting angle 21a, in which the sitting position of the sitting element 36a changes from the first sitting position to the second sitting position, may vary. As the range can be very small, the person 11a sitting on the sitting posture assisting device 10a may have the impression that the sitting position of the sitting element 36a tilts at a certain sitting angle 21a. In a preferred embodiment, the range in which the sitting position changes is set between a sitting angle 21a of 40 degrees and a sitting angle 21a of 50 degrees.

The sitting element 36a is designed to be arranged in the different sitting positions with respect to the frame means 27a. If the person 11a wearing the sitting posture assisting device 10a is sitting or partly sitting on the sitting posture assisting device 10a, the sitting element 36a is in close contact to the thigh and/or the buttock of the person 11a. If the person 11a wearing the sitting posture assisting device 10a is sitting, the portion 37a of the seat surface 28a having the flat shape is substantially parallel to the thigh of the person 11a. This is in particular the case if the sitting angle 21a between the upper support 13a and the lower support 14a is greater than 50 degrees and less than 90 degrees. In particular, the thigh of the person 11a is then in contact with the portion 37a of the seat surface 28a formed by the sitting element 36a, having the flat shape. If the sitting angle 21a is smaller, especially less than 40a degrees, the buttock of the person 11a comes into contact with the portion 38a of the seat surface 28a having the bent shape.

The lower support 14a comprises a base frame 46a and the foot connection unit 20a connected to the base frame 46a (cf. FIG. 2). The base frame 46a forms a second joint element for the joint 16a connecting the upper support 13a and the lower support 14a. The second blocking element 23a of the blocking means 17a is connected to the base frame 46a of the lower support 14a.

At least a portion of the foot connection unit 20a is rotatable relative to the base frame 46a. The foot connection unit 20a comprises a shoe connector 47a, which is rotatable with respect to the base frame 46a. The foot connection unit 20a comprises a ground contact element 48a, which is mounted on the base frame 46a, and a rotatable connection 49a, which arranges the shoe connector 47a in such a way that it is rotatable with respect to the base frame 46a. The rotatable connection 49a has at least two axes 50a, 51a, which are perpendicular to each other. The first axis 50a is orientated radially with respect to the axis of the joint 16a. The second axis 51a is orientated in parallel to the axis of the joint 16a.

The shoe connector 47a, which is intended for fixing the shoe of the person 11a wearing the sitting posture assisting device 10a, comprises a shoe strapping element 52a and a mounting bracket 53a, which are movably connected to each other (cf. FIG. 1). The strapping element 52a and the mounting bracket 53a in combination are intended for fixing the person's 11a shoe. The shoe strapping element 52a is rotatable with respect to the mounting bracket 53a around an axis 54a which is parallel to the second axis 51a of the rotatable connection 49a of the foot connection unit 20a. Due to at least a part of the foot connection unit 20a being rotatable relative to the base frame 46a, the shoe connector 47a can follow the movement of the foot and/or shoe of the person 11a wearing the sitting posture assisting device 10a. The ground contact element 48a is designed to come into contact with the ground 15a when the person 11a is sitting or partly sitting. Thus, the weight force of the person 11a is transmitted to the ground 15a. As the upper support 13a is connected to the thigh of the person 11a, the ground contact element 48a loses the contact to the ground 15a when the person 11a wearing the sitting posture assisting device 10a is standing or walking. Due to the rotatable connection 49a of the shoe connector 47a, the lower support 13a is intended for being lifted with reference to the mounting bracket 53a.

The shoe strapping element 52a can optionally be adjustably connected to the mounting bracket 53a, on account of which the shoe strapping element 52a can be adjusted to the shoe of the person 11a wearing the sitting posture assisting device 10a. The mounting bracket 53a may feature a clipping area, where the shoe strapping element 52a can be clipped to the mounting bracket 53a in at least two different positions. Thus, the shoe connector 47a can be adjusted to a length of the foot and/or shoe of the person 11a wearing the sitting posture assisting device 10a.

The shoe strapping element 52a features a center part, which at least partly comes into contact with the mounting bracket 53a when the shoe strapping element 52a is connected to the mounting bracket 53a. The center part consists of a brace, which ends in one strap mount at each of its ends. The shoe strapping element 52a is connected to the mounting bracket 53a via the strap mounts. In this way the shoe strapping element 52a is rotatably connected to the mounting bracket 53a. In another embodiment the mounting bracket 53a of the shoe connector 47a can be one-sided.

The entire shoe connector 47a is disconnectable from the ground contact element 48a. A portion of the rotatable connection 49a between the shoe connector 47a and the ground contact element 48a, implementing the second axis 51a, is designed as a quick-release fastener. When connecting the shoe connector 47a to the shoe of the person 11a, the entire shoe connector 47a may be disconnected from the base frame 46a of the lower support 14a. When the shoe strapping element 52a and/or the mounting bracket 53a has been adjusted to the shoe of the person 11a and the shoe connector 47a is connected with the person's 11a shoe, the shoe connector 47a can be connected to the ground contact element 48a. In addition, the shoe connector 47a can be replaced when it is worn down.

In the shown embodiment, the ground contact element 48a comprises a ground contact surface, which is designed to be placed on the ground 15a, to transmit the person's 11a weight force to the ground 15a. In another embodiment the rotatable connection 49a between the ground contact element 48a and the shoe connector 47a may be designed to transmit the person's 11a weight force. When the person 11a is sitting or partly sitting on the sitting posture assisting device 10a, the weight force is transmitted to the shoe connector 47a via the ground contact element 48a. The weight force is then transmitted from the shoe connector 47a to the ground 15a either directly or via the shoe of the person 11a.

The leg unit 12a comprises an actuator 55a, which is designed to control the blocking means 17a. In the shown embodiment, the blocking means 17a comprises a valve designed to be closed by the actuator 55a. The actuator 55a is designed as an electromotor which is able to open and to close the valve.

The wearable sitting posture assisting device 10a comprises a control unit 57a, which is designed to control the two blocking means 17a of the two leg units 12a, 12'a. The control unit 57a is designed to control the two blockings means 17a in combination. The actuators 55a of the two leg units 12a, 12'a are connected to the control unit 57a. The control unit 57a is designed to control the leg units 12a, 12'a in combination or separately. Each of the leg units 12a, 12'a may comprise a sitting angle sensor, wherein the control unit 57a is preferably designed to control the blocking means 17a depending on a sensor signal of the respective sitting angle sensor.

To control one of the leg units 12a, 12'a separately or in combination, the blocking function is designed to differentiate between a movement and an idle state of the respective leg unit 12a, 12'a by analyzing the sensor signal. The blocking function is designed to block and to unblock the blocking means 17a of the respective leg unit 12a, 12'a. The control unit 57a has a manual-blocking mode, in which the control unit 57a blocks or unblocks the blocking means 17a of the respective leg unit 12a, 12'a in dependence of an input signal of the person 11a. If both leg units 12a, 12'a are connected to the control unit 57a, the blocking means 17a of both leg units 12a, 12'a are blocked at the same time.

The control unit 57a is attached to the body wearing unit 19a. The body wearing unit 19a comprises a mount 61a, in which the control unit 57a is mounted, the mount 61a providing an electrical connection to the leg units 12a, 12a. As the leg units 12a, 12'a are equivalent, a sequence and an arrangement of connecting the leg units 12a, 12'a to the control unit 57a is insignificant. Each of the leg units 12a, 12'a can be worn on the left leg or on the right leg. In this way, the two leg units 12a. 12'a are equivalent and the control unit 57a is separated from the leg units 12a, 12'a. The wearable sitting posture assisting device 10a is designed in a modular manner. The control unit 57a, the body wearing unit 19a and each of the leg units 12a. 12'a can be replaced separately.

The wearable sitting posture assisting device 10a comprises the body wearing unit 19a, which is in particular provided to increase a wearing comfort. The body wearing unit 19a comprises at least a waist belt unit 62a. In the shown embodiment, the body wearing unit 19a comprises in addition a shoulder belt unit 63a. The leg units 12a, 12'a are attached to the waist belt unit 62a. Each of the leg units 12a, 12'a comprises a strap 64a providing a mechanical connection of the upper support 13a with the waist belt unit 62a, and comprises a strap connector 65a rendering the mechanical connection detachable. The strap connection 65a is embodied in a one-part implementation with an electrical connector, which is designed to connect the actuator 55a and the sitting angle sensor of the respective leg unit 12a to the control unit 57a. In this way, the mechanical connection and the electrical connection are provided to be attached and detached together.

The leg unit 12a comprises a guiding means 29a for the blocking means 17a, which guiding means 29a is designed to allow a rotation of the joint 16a while the blocking means 17a is in the blocked state (cf. FIGS. 3 to 5). In the blocked state the blocking means 17a defines the sitting angle 21a for the at least partly sitting posture. The guiding means 29a provides a degree of freedom of movement of the joint 16a connecting the supports 13a, 14a while the blocking means 17a is in the blocked state. At the same time the guiding means 29a limits the movement of the joint 16a to a range spanned by the sitting angle 21a, which the blocking means 17a is blocked at, and the standing posture, which corresponds to a sitting angle 21a of zero degrees.

The blocking means 17a has an adjustable length provided to define the at least partly sitting posture. The length of the blocking means 17a is defined by a position of the two blocking elements 22a, 23a with respect to each other. In the blocked state, the length of the blocking means 17a is fixed. In the unblocked state, the two blocking elements 22a, 23a are linearly movable to each other. The blocking means 17a has a main extension direction, along which the blocking elements 22a, 23a are movable with respect to each other in the unblocked state. The blocking means 17a is arranged between the upper support 13a and the lower support 14a.

The upper support 13a comprises a pivot element 30a, on which the blocking means 17a is swivel-mounted. The pivot element 30a defines an axis which is oriented perpendicular to the main extension direction of the blocking means 17a. The pivot element 30a connects one of the blocking elements 22a, 23a to the upper support 13a. Along the main extension direction of the blocking means 17a, the blocking element 22a is rigidly connected to the upper support 13a. The pivot element 30a allows a rotation of the blocking element 22a with respect to the upper support 13a when the sitting angle 21a changes.

The lower support 14a comprises a pivot element 39a, on which the guiding means 29a is swivel-mounted. The pivot element 39a defines an axis which is parallel to the axis of pivot element 30a of the upper support 13a. The pivot element 39a connects the guiding means 29a to the lower support 14a. The second blocking element 23a of the blocking means 17a is connected to the lower support 14a via the guiding means 29a and the pivot element 39a.

The guiding means 29a provides a movability of the blocking means 17a with respect to the lower support 14a. In the blocked state, in which the two blocking elements 22a, 23a are rigidly connected to each other, the guiding means 29a provides the movability which is necessary to change the sitting angle 21a. The guiding means 29a provides a functionality which is similar to a functionality of the blockings means 17a in the unblocked state. Differently from the blocking means 17a, the movability provided by the guiding means 29a is not adjustable by the person 11a wearing the sitting posture assisting device 10a.

The guiding means 29a has a lower end stop 32a provided to limit the rotation of the joint 16a to the sitting angle 21a the blocking means 17a has been adjusted to. If the blocking means 17a is blocked at a certain sitting angle 21a, the guiding means 29a allows a movement of the knee joint 16a within a range limited by the sitting angle 21a of zero degrees, which corresponds to the standing posture, on the one hand and by the sitting angle 21a, which is defined by the blocking means 17a, on the other hand. As the movability of the guiding means 29a is independent from the state of the blocking means 17a, the sitting angle 21a can be stored in the blocking means 17a by keeping the blocking means 27a in the blocked state. The guiding means 29a allows the person 11a wearing the sitting posture assisting device 10a to walk while the blocking means 17a is in the blocked state. The end stop 32a of the guiding means 29a restricts the movement of the knee joint 16a to the sitting angle 21a if the blocking means 17a is in the blocked state.

The leg unit 12a has an expansion element 33a, which is provided to tension the blocking means 17a between the end stop 32a of the guiding means 29a and the pivot element 30a of the upper support 13a. The expansion element 33a is integrated in the blocking means 17a. The expansion element 33a is preferably implemented by a spring. Other embodiments, especially embodiments comprising an actuator like an electromotor, are also conceivable. The expansion element 33a is provided to expand the blocking means 17a when the sitting angle 21a increases while the blocking means 17a is in the unblocked state. Due to the expansion element 33a, the blocking means 17a while in the unblocked state is permanently in contact with the end stop 32a. In the shown embodiment the expansion element 33a is incorporated by the blocking elements 22a, 23a of the blocking means 17a.

The guiding means 29a is provided for reducing the sitting angle 21a if the person 11a wearing the sitting posture assisting device 10a gets up without unblocking the blocking means 17a. The guiding means 29a has a linear guide 34a designed to connect the blocking means 17a and the lower support 14a to each other. The linear guide 34a is provided to guide the second blocking element 23a of the blocking means 17a with respect to the lower support 14a. In combination with the pivot element 39a the linear guide 34a connects the blocking means 17a to the lower support 14a movably and pivotably.

The linear guide 34a has a contacting surface, which is provided for the blocking means 17a and serves as the end stop 32a provided to limit the rotation of the joint 16a. The guiding means 29a is formed like a piston-cylinder-system which provides the movability along the main extension direction of the blocking means 17a. The guiding means 29a has a guiding element 35a, which is pivotably connected to one of the supports 13a, 14a, providing the linear guide 34a for the blocking means 17a. The guiding element 35a acts as the cylinder, while the second blocking element 23a of the blocking means 17a acts as the piston. The guiding element 35a provides the contacting surface which serves as the end stop 32a. The guiding element 35a is formed as a hollow cylinder having an end plate at one of its ends. The linear guide 34a has a main extension direction orientated in parallel to the main extension direction of the blocking means 17a. The guiding element 35a is swivel-mounted on the pivot element 39a of the lower support 14a.

In FIGS. 6 to 8 a further exemplary embodiment of the invention is shown. The following description is substantially restricted to the differences between the exemplary embodiments wherein, regarding structural components, features and functions, the description of the exemplary embodiment of FIGS. 1 to 5 may be referred to. For distinguishing the exemplary embodiments, the letter a in the reference numerals of the exemplary embodiment of FIGS. 1 and 2 has been replaced by the letter b in the reference numerals of FIG. 3. Regarding structural components having the same denomination, in particular structural components with the same reference numerals, principally the drawings and/or the description of the exemplary embodiment of FIGS. 1 and 2 may be referred to.

FIGS. 6 to 8 show a second embodiment of a leg unit 12b for a wearable sitting posture assisting device at different sitting angles. The leg unit 12b comprises an upper support 13b designed to receive a weight force of a person and a lower support 14b designed to transmit the person's weight force to a ground. Furthermore the leg unit 12b has a joint 16b, which connects the two supports 13b, 14b to each other, and a blocking means 17b, which implements a blocked state to block the joint 16b, and an unblocked state, in which the joint 16b is fully movable. In addition the leg unit 12b has a guiding means 29b for the blocking means 17b, which guiding means 29b is designed to allow a rotation of the joint 16b while the blocking means 17b is in the blocked state.

The leg unit 12b differs from the previous embodiment in particular in an implementation of the guiding means 29b. The guiding means 29b has a linear guide 34b designed to connect the blocking means 17b and the lower support 14b to each other. The lower support 14b has a base frame 46b providing the linear guide 34b. The linear guide 34b is designed as a groove formed by the base frame 46b of the lower support 14b. The linear guide 34b has a main extension direction which is at least substantially parallel to a main extension direction of the lower support 14b. The blocking means 17b has a second blocking element 23b, which is connected to the lower support 14b by the linear guide 34b movably and pivotably. In this way the guiding means 29b integrally forms a pivot element 39b of the lower support 14b, which pivot element 39b connects the blocking element 23b of the blocking means 17b and the lower support 14b to each other in a swivel-mounted fashion.

The invention claimed is:

1. A leg unit for a wearable sitting posture assisting device, comprising:
   an upper support designed to receive a weight force of a person, a lower support designed to transmit the weight force of the person to a ground, a joint connecting the at least two supports to each other, a blocking means implementing a blocked state to block the joint at at least one sitting angle corresponding to an at least partly sitting posture, and
   a guiding means for the blocking means designed to allow a rotation of the joint while the blocking means is in the blocked state, wherein
   the blocking means has an adjustable length provided to define the at least partly sitting posture.

2. The leg unit according to claim 1, wherein
   in the blocked state, the length of the blocking means is at least substantially fixed.

3. The leg unit according to claim 1, wherein
   one of the supports comprises a pivot element, on which the blocking means is swivel-mounted.

4. The leg unit according to claim 3,
   wherein the guiding means comprises at least one end stop provided to limit the rotation of the joint to the sitting angle which the blocking means is adjusted to, and comprising
   an expansion element which is provided to tension the blocking means between the end stop of the guiding means and the pivot element.

5. The leg unit according to claim 1, wherein
   the guiding means comprises at least one end stop provided to limit the rotation of the joint to the sitting angle which the blocking means is adjusted to.

6. The leg unit according to claim 5,
   wherein the guiding means comprises at least one linear guide designed to connect the blocking means and one of the supports with each other, wherein
   the linear guide comprises at least one contacting surface, which is provided for the blocking means and serves as the end stop provided for limiting the rotation of the joint.

7. The leg unit according to claim 1, wherein
   the guiding means is provided for reducing the sitting angle.

8. The leg unit according to claim 1, wherein
   the guiding means comprises at least one linear guide designed to connect the blocking means and one of the supports with each other.

9. The leg unit according to claim 8, wherein
   the guiding means comprises a guiding element, which is pivotably connected to one of the supports, providing the linear guide for the blocking means.

10. The leg unit according to claim 9, wherein
    the linear guide has a main extension direction orientated in parallel to a main extension direction of the blocking means.

11. The leg unit according to claim 9, wherein
    the blocking means comprises at least two blocking elements, wherein one of them is swivel-mounted on one of the supports and another one of them is linearly movable connected with the guiding element.

12. The leg unit according to claim 8, wherein
    one of the supports comprises a base frame providing the linear guide, by which the blocking means is connected to the support movably and pivotably.

13. A wearable sitting posture assisting device, comprising two leg units according to claim 1.

14. A method to block a wearable sitting posture assisting device in an at least partly sitting posture, comprising:
    providing a leg unit for the wearable sitting posture assisting device that comprises an upper support designed to receive a weight force of a person, a lower support designed to transmit the weight force of the person to a ground, a joint connecting the at least two supports to each other, a blocking means that implements a blocked state to block the joint at at least one sitting angle corresponding to the at least partly sitting posture, and a guiding means for the blocking means designed to allow a rotation of the joint while the blocking means is in the blocked state, wherein the blocking means has an adjustable length provided to define the at least partly sitting posture;
    blocking, via the blocking means, the joint in the at least partly sitting posture, the joint connecting the upper support to the lower support; and
    allowing a rotation of the joint while the blocking means is in the blocked state via the guiding means for the blocking means.

15. The method according to claim 14, further comprising providing a further leg unit.

* * * * *